(12) United States Patent
Chatterjee et al.

(10) Patent No.: US 6,828,130 B2
(45) Date of Patent: Dec. 7, 2004

(54) PRODUCTION OF GLUCONATE SALTS

(75) Inventors: Chinmay Chatterjee, Brighton, MA (US); Nilu Prasad Chatterjee, Brighton, MA (US); Edward D. Furtado, Leominster, MA (US)

(73) Assignee: NEC Partnership, Brighton, MA (US)

( * ) Notice: Subject to any disclaimer, the term of this patent is extended or adjusted under 35 U.S.C. 154(b) by 258 days.

(21) Appl. No.: 10/142,499

(22) Filed: May 10, 2002

(65) Prior Publication Data

US 2002/0127665 A1 Sep. 12, 2002

Related U.S. Application Data

(62) Division of application No. 09/863,018, filed on May 22, 2001, now Pat. No. 6,416,981.
(60) Provisional application No. 60/206,421, filed on May 23, 2000.

(51) Int. Cl.⁷ .................................................. C12P 7/58
(52) U.S. Cl. ........................................................ 435/137
(58) Field of Search ............................................ 435/137

(56) References Cited

U.S. PATENT DOCUMENTS

| | | | |
|---|---|---|---|
| 3,454,501 A | 7/1969 | Ziffer et al. | 252/142 |
| 3,670,000 A | 6/1972 | Zeiss | 556/149 |
| 3,935,071 A | 1/1976 | Bergmeyer et al. | 195/32 |
| 3,953,296 A | 4/1976 | Trutnovsky et al. | 195/103 |
| 4,345,031 A | 8/1982 | Coppens | 435/137 |
| 4,460,686 A | 7/1984 | Hartmeier | 435/137 |
| 4,618,601 A | 10/1986 | Chazot et al. | 514/23 |
| 4,755,467 A | 7/1988 | Scopes et al. | 435/125 |
| 5,897,995 A | 4/1999 | Vroemen et al. | 435/137 |
| 6,100,297 A | 8/2000 | Weglicki | 514/557 |
| 6,416,981 B1 | 7/2002 | Chatterjee et al. | 435/137 |

FOREIGN PATENT DOCUMENTS

| | | |
|---|---|---|
| RU | 2118955 | 9/1998 |
| WO | WO 96/35800 | 11/1996 |
| WO | WO9817237 | 4/1998 |
| WO | WO09915673 | 4/1999 |
| WO | WO0013649 | 3/2000 |
| WO | WO0038657 | 7/2000 |

OTHER PUBLICATIONS

US 5,998,179, 12/1999, Lantero et al. (withdrawn)
Bentley, et al., "The Mechanism of the Action of Notatin", *The Journal of Biochemistry*, vol. 45, pp. 584–590, (1949).
Nakamura et al., "Kinetic Studies on the Action of Glucose Oxidase", *The Journal of Biochemistry*, vol. 52, No. 3, pp. 214–220, (1962).
Nakamura, et al.,"Absorption Spectrum of Flavin Mononucleotide Semiquinone", *The Journal of Biochemistry*, vol. 53, No. 2, pp. 143–146, (1963).
Gibson et al., "Kinetics and Mechanism of Action of Glucose Oxidase", *The Journal of Biological Chemistry*, vol. 239, No. 11, pp. 3927–3934 (1964).
Weibel, et al., "The Glucose Oxidase Mechanism". *The Journal of Biological Chemistry*, vol. 246, pp. 2734–2744 (1971).
Greenfield et al., "Inactivation of Immobilized Glucose Oxidase by Hydrogen Peroxide", *Analytical Biochemistry*, vol. 65, pp. 109–124, (1975).

*Primary Examiner*—Herbert J. Lilling
(74) *Attorney, Agent, or Firm*—Bromberg & Sunstein LLP

(57) ABSTRACT

A method for producing substantially pure ammonium gluconate or metal gluconate that includes separating reagents for reuse from the enzymatically converted gluconate by ultrafiltration

41 Claims, 2 Drawing Sheets

PRODUCTION OF GLUCONATE SALTS

CROSS REFERENCE TO RELATED APPLICATIONS

This application is a divisional of U.S. patent application Ser. No. 09/863,018 filed May 22, 2001 now U.S. Pat. No. 6,416,981, claiming priority from U.S. Patent application No. 60/206,421 filed May 23, 2000. All of these applications are incorporated herein by reference.

TECHNICAL FIELD AND BACKGROUND ART

The description relates to the production of ammonium gluconate in a process that involves ultrafiltration. The process utilizes relatively small amounts of reactants that result in an overall reduction in cost that is significant for large scale manufacture of gluconate.

BACKGROUND

The demand for metal gluconates is increasing due to their multiple applications in different industries. For example, sodium gluconate has utility as an environmentally friendly industrial detergent and calcium gluconate can be used for dietary calcium supplementation. Ferrous gluconate is used for iron supplementation of anemic patient while zinc gluconate is used as a zinc supplement in nutritional diets.

Current production techniques are directed to the manufacture of gluconic acid and sodium gluconate. The present production protocols tend to use relatively large amounts of costly starting materials. Inefficiencies in product purification result from relatively wasteful purification procedures that are required to remove residual reactants from the gluconic acid or sodium gluconate during manufacture. Moreover, present techniques are associated with inactivation of reagent enzymes when used.

Currently gluconic acid and its salts are produced by batch fermentation or using enzymes (U.S. Pat. No. 5,897,995). Batch fermentation utilizes *Aspergillus niger* that converts glucose to gluconic acid and its salts. (Greenfield, Paul F., Kittrell, James, R., Laurence, Robert L., (1975) "Inactivation of Immobilized Glucose Oxidase by Hydrogen Peroxide", Anal. Biochem., 65, PP 109–124. Weibel, Michael K., Bright, Harold J., (1971) "The Glucose Oxidase Mechanism", J. Biol. Chem., Vol. 246, May 10, pp 2734–2744. Gibson, Quesntin H., Swoboda, Bennett E. P., Massey, Vincent, (1964) "Kinetics and Mechanism of Action of Glucose Oxidase", J. Biol. Chem., Vol. 239, No. 11, pp 3927–3934. Nakamura, T., and Ogura, Y. L., (1963) J. Biolchem (Tokyo), 53, 2, pp 143. Nakamura, T., and Ogura, Y. L., (1962) J. Biolchem (Tokyo), 52, 3, pp 214. Bentley, R., and Neuberger, A., (1949) Biochem. J., 45, pp 584.) Some of the problems associated with fermentation production techniques include the use of complex media for growing microorganisms and associated increased complexity of purification Enzymatic production of gluconic acid or its salts tend to rely on relatively large amounts of reagents (U.S. Pat. No. 5,897,995 describes the use of glucose reagent at a concentration of at least 10% and preferably as high as 50%). U.S. Pat. No. 3,935,071 describes the conversion of glucose into gluconic acid using enzymes bound to a carrier (also FRA2 2029645, EP 017708) and separation of the gluconic acid by anion exchange chromatography.

In summary, the existing processes for the production of gluconates are cost inefficient for reasons that include: (a) use of excess costly starting materials and; (b) loss of product through purification procedures.

The inefficiencies and costs of current production techniques for gluconates are magnified during large scale production. Each reaction vessel or fermentor in the manufacture of gluconic acid may have a capacity of greater than 100,000 liters and multiple fermentors of this size are required to produce millions of pounds of gluconates. Any reduction in raw materials or handling would result in a significant cost reduction.

In addition to the cost of materials, existing production of gluconates generates substantial amounts of waste materials. Each production batch can generate millions of gallons of industrial as well as biological wastes. The large amount of industrial and biological wastes generated from conventional fermentation processes can pollute the city sewage system if the plant effluents are not treated extensively. Thus, the conventional fermentation process puts large burden to the city infrastructure of any community due to its large resource requirements and waste treatment facilities. Due to the increased demand of environmentally benign gluconates in industrial and pharmaceutical applications, any improvement in the cost and efficiency of production methods would be desirable.

SUMMARY OF THE INVENTION

In preferred embodiments of the invention, a method is provided for producing substantially pure ammonium gluconate, that includes the steps of (a) adding a first volume of a glucose solution in a glucose feed to a preparation of glucose oxidase in a reaction chamber and adding a second volume of ammonia in an ammonium feed to the reaction chamber for forming a reaction mixture containing ammonium gluconate; (b) removing a third volume of the reaction mixture; and (c) separating ammonium gluconate from the third volume by ultrafiltration to produce substantially pure ammonium gluconate. In a preferred embodiment of the invention, the preparation in the reaction chamber further includes catalase. The ammonia optionally is in liquid form or in gaseous form. The ammonium gluconate may be separated from the third volume removed from the reaction mixture through an ultrafiltration membrane to provide a retentate for returning to the reaction chamber and a permeate containing ammonium gluconate. The ammonium gluconate may be crystallized from the permeate. The glucose oxidase and/or catalase may be derived from a microorganism, for example, *Aspergillus niger*.

Concerning amounts of reactant and catalyst, the glucose oxidase activity per unit weight of glucose may be maintained at less than 20 and optionally catalase activity per unit weight of glucose may be less than 800. A ratio of glucose oxidase to catalase activity may be less than 0.1. The reaction chamber may be maintained at a temperature of between 150 C. and 400 C. and the reaction occurs in the presence of oxygen of atmospheric air and optionally at a pH in the range of pH 4 to pH 8, for example pH 5 to pH 7. The concentration of glucose in the continuous feed may be maintained at less than 75% (w/v) in the reaction mixture and the concentration of glucose in the reaction chamber is maintained at less than about 10% (w/v) for example, less than 5% in the reaction mixture. The ammonia in the second volume has a concentration of 5%–30% (v/v). The ultrafiltration membrane may optionally have a pore size of molecular weight cut-off between 5,000 and 50,000.

In a preferred embodiment, glucose may have a conversion efficiency into ammonium gluconate of at least 90%.

In a preferred embodiment, a method for producing metal gluconates is provided that includes (a) adding a first volume of a glucose solution in a glucose feed to a preparation of glucose oxidase in a reaction chamber and adding a second volume of a metal base solution or suspension in a feed to the reaction chamber for forming a reaction mixture containing metal gluconate; (b) removing a third volume of the reaction mixture; and (c) separating metal gluconate from the third volume by ultrafiltration to produce substantially pure metal gluconate.

Accordingly, the metal gluconate may be crystallized from the permeate after ultrafiltration of the third volume. The metal base solution may be selected from the group consisting of sodium base, potassium base, calcium base, zinc base, ferrous base, magnesium base, manganese base and cuprous base solution and further may include a lithium base.

LIST OF FIGURES

The foregoing and other objects and advantages of the invention will be more fully appreciated from the following description thereof with reference to the accompanying drawings, wherein.

DETAILED DESCRIPTION

Embodiments of the present invention are directed toward an improved method of producing ammonium gluconate, from which a person of ordinary skill in this art can produce other gluconates (e.g., sodium, potassium, lithium, calcium, magnesium, manganese, iron, zinc, etc.) by reacting ammonium gluconate with a metal base solution. Accordingly, the method does not rely on fermentation but instead utilizes reagents to catalyze the conversion of glucose to ammonium gluconate. In an embodiment of the invention, the catalysts are enzyme reagents which are preferably in a soluble form in the reaction chamber. The term "reagent" used herein applies to any of glucose, base or catalysts.

Figure 1:
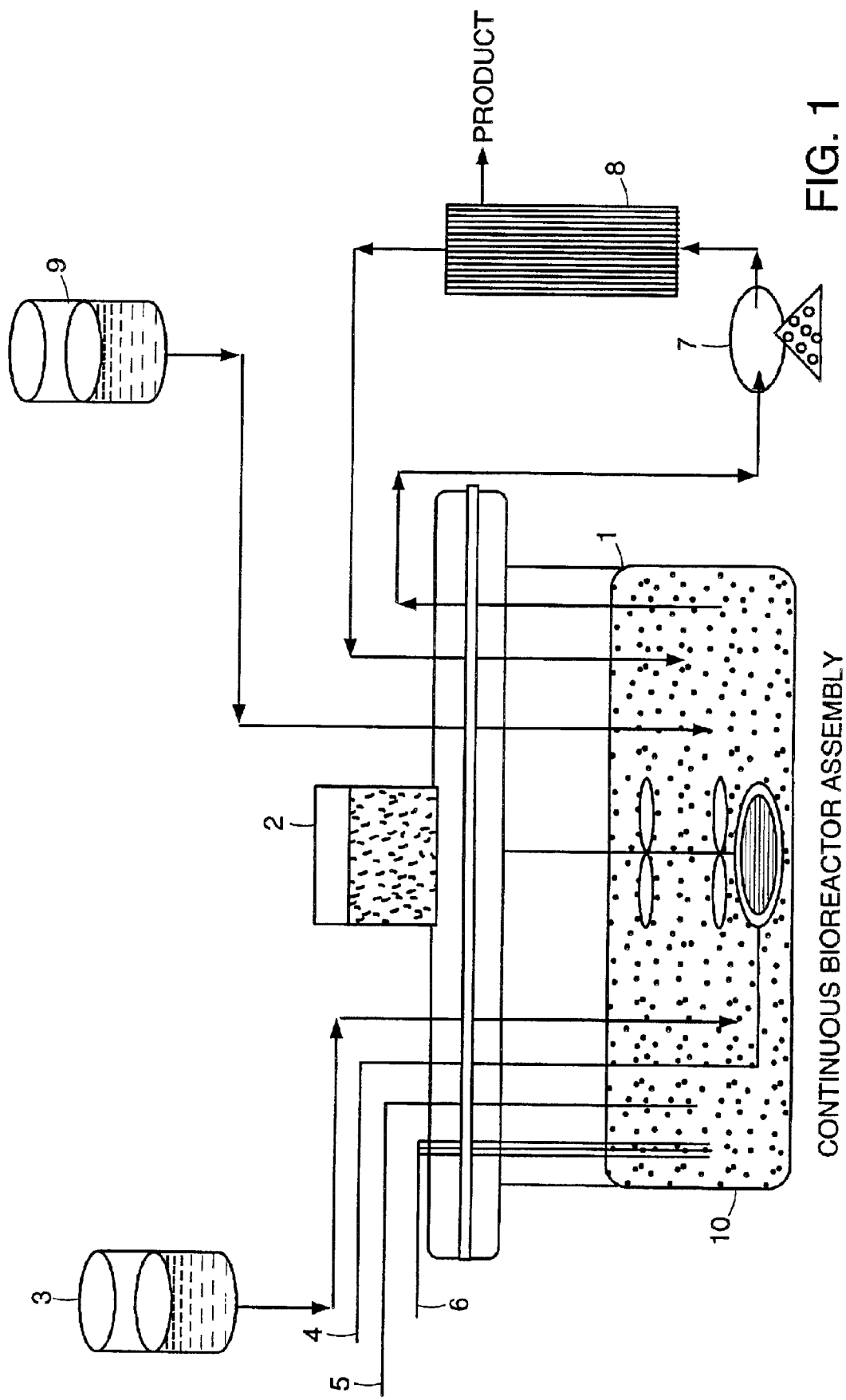
FIG. 1 shows a flow diagram for the process of making gluconate salts by a continuous process.

The method requires the use of glucose oxidase as a catalyst to form gluconate from glucose and may optionally include catalase to react with hydrogen peroxide. Other reagents known in the art, for example metals including any of nickel, platinum or silver, may be used in an insoluble form to react with hydrogen peroxide in place of or in addition to catalase. An embodiment of the method of the invention illustrated by a schematic diagram of bioreactor assembly is shown in FIG. 1. The bioreactor assembly includes the following components: (1) a computerized bioreactor assembly with reaction mixture, (2) an agitator assembly, (3) liquor ammonia storage container, (4) air sparger assembly, (5) temperature sensor, (6) pH sensor, (7) circulation pump, (8) ultrafiltration cartridge, (9) Glucose feed storage container and (10) reaction chamber. In FIG. 1, the reaction mixture includes glucose oxidase and catalase as catalysts in the reaction chamber (10) into which glucose (9) and liquid ammonia (3) is continuously added via feed tubing from reagent storage containers (or feed reservoirs) to form a reaction mixture. Although liquid ammonia is used in FIG. 1, gaseous ammonia may also be used and passed by feed tubing into the reaction chamber. The term "ammonia" as used here and in the claims is defined as ammonia gas or liquid ammonia solution. The reaction mixture is continuously removed from the reaction chamber, and passed by means of a circulation pump (7) through an ultrafiltration unit (8) and recycled back into the reaction chamber (10) through the retentate portal (14) shown in FIG. 2. The volume of reaction mixture (third volume) that is continuously removed from the reaction chamber may be equivalent to the volume of reactants including but not limited to a first volume of glucose and a second volume of ammonia which is introduced into the reaction chamber.

There may be circumstances when the volume of materials entering the reaction chamber is different from the volume of reaction mixture removed from the reaction chamber. For example, a fed-batch system may be used in which reagents are introduced continuously until interrupted to permit the accumulated product with reaction mixture to be removed from the reaction chamber. The rate at which the reagents accumulate and the periods during which the product is removed is determined by the reaction rate. The separation step for the fed-batch system is substantially similar to that of the continuous system. An additional alternative to the continuous system for the production of ammonium gluconate is the use of a batch system for producing ammonium gluconate. Accordingly, reagents are introduced into a reaction chamber, the reaction is permitted to proceed and the ammonium gluconate product is purified from the entire volume contained in the reaction chamber. The separation procedure described below is applicable to any of the continuous, fed-batch or batch systems for producing ammonium gluconate.

Figure 2:
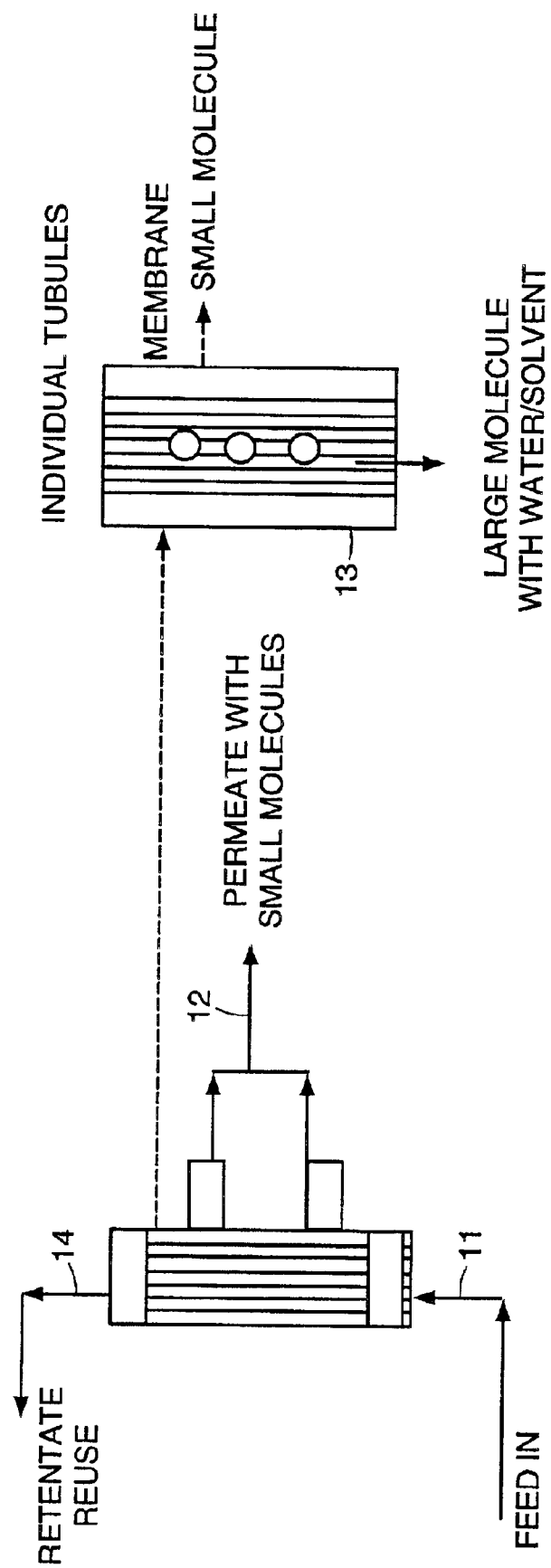
FIG. 2 shows tangential flow filtration using cylindrical cartridges with flow path of permeate (including ammonium gluconate) and retentate containing enzymes for recycling with scale up of individual tubules in the filtration unit.

As illustrated in FIGS. 1 and 2, ammonium gluconate present in the reaction mixture is separated from the reaction mixture in an ultrafiltration unit (8) and passed to a collection chamber. The ultrafiltration membrane separates the enzyme mixture from the soluble smaller ammonium gluconate molecules. These ultrafiltration membranes may have a molecular cut-off between 300 to 100,000 more particularly 5,000 to 50,000 and may be contained in an ultrafiltration cartridge. The ultrafiltration cartridge contains multiple membrane tubules packed in a bundle with an inlet and an outlet for retentates and permeates (FIG. 2). Reaction media from the reaction chamber enters the ultrafiltration cartridge through a Feed-In inlet (11) and passes through tubules (13) before exiting through the Retentate outlet (14). During flow-through, small molecules in solution are caused to pass through membranes and are collected as a Permeate (12) from which ammonium gluconate is subsequently crystallized. Larger molecules including the enzymes used in the procedure are retained by the membranes and are passed back into the reaction chamber in the water/solvent to continue the reaction in a continuous or fed-batch production or to initiate a batch synthesis in a batch process. Any residual glucose in the permeate is separated from ammonium gluconate during crystallization. The collection of crystals of ammonium gluconate represents a substantially pure preparation of ammonium gluconate.

The ammonium gluconate in solution or in crystallized form may be used for any of a number of processes including the formation of other metal gluconates. These may be made using simple chemical reactions known to any person skilled in the art. Examples of metal gluconates include: sodium gluconate, potassium gluconate, lithium gluconate, calcium gluconate, zinc gluconate, ferrous gluconate, magnesium gluconate, manganese gluconate and cuprous gluconate.

Alternatively, metal gluconates may be made directly by a continuous process, fed batch process or batch process that utilizes enzymes and where the reaction media is passed through an ultrafiltration unit in a similar manner to that disclosed for ammonium gluconate. Accordingly, the storage containers will contain glucose and a base solution of the metal for reacting with the glucose to form the metal gluconate. The metal gluconate may be crystallized from the permeate.

In an embodiment of the invention, the reaction is started with a solution containing less than 75% (w/v) glucose in the glucose feed storage container, also referred to as the "glucose feed", so as to provide a concentration of 5% (w/v) or less, in the reaction chamber. The glucose oxidase or enzyme mixture is added to the reaction mixture prior to start of operation. The reactor is connected with an ammonia feed tubing, air flow meter and glucose solution feed tubing.

After reaching steady state, the reaction mixture is continuously recirculated through the ultrafiltration membrane. The flow of materials may be computer regulated to ensure that an appropriate range of concentration of substrates as well as pH, temperature, oxygenation and enzyme concentrations are maintained through proper regulation of flow rates.

The enzymes utilized in the reaction may be prepared by methods that are well known in the art or may be obtained commercially. For example, glucose oxidase and catalase may be obtained as a mixture (Hidelase enzyme mixture) from Amano Enzyme Company, Ltd., USA. The Hidelase enzyme mixture contains glucose oxidase and catalase obtained from fungal fermentation of *Aspergillus niger* containing on average 1.2% (0.9–1.5%) glucose oxidase and 3% catalase. Glucose oxidase and catalase may be obtained from separate or the same sources including sources other than *Aspergillus niger*. The activity of enzyme glucose oxidase and catalase suitable for use in the production of gluconate is measured in units of enzyme activity. One unit of glucose oxidase activity is defined as the amount of enzyme that can produce 1 μmol of gluconic acid and 1 μmol of hydrogen peroxide ($H_2O_2$) in 1 minute at 25° C. and pH 7. Similarly, one unit of catalase activity is defined as the amount of enzyme that will catalyze to convert 1 μmol of hydrogen peroxide ($H_2O_2$) to produce ½ μmol of each water and oxygen in 1 minute at 25° C. and pH 7. Accordingly, in an embodiment of the invention, the enzyme mixture has activity such that glucose oxidase activity is 15,000 units per gram of pure enzyme and catalase activity is 300,000 units per gram of pure enzyme as per the manufacturer's specification. Under steady state conditions the ratio of glucose oxidase to grams of glucose present in the reaction mixture may be maintained at a ratio of less than 20. Similarly, under steady state reaction condition the ratio of catalase to grams of glucose present in the reaction mixture may be maintained at less than 800. We have observed that if these ratios are maintained then the ratio between the glucose oxidase and catalase varies between 0.01 and 0.1. These ratios are calculated under steady state conditions based on the actual enzymatic protein present in the reaction mixture as specified by the manufacturer.

The glucose is fed from storage container to the reaction chamber containing the enzyme. The concentration of glucose in the glucose feed storage container is maintained at between 20–75% (w/v). The glucose may be prepared from pure dextrose powder or crystals or dextrose syrup. The glucose feed to the reaction mixture is controlled in such a way that the glucose concentration in the reaction mixture does not exceed the appropriate amount (less than 10% for example, 5% (w/v)). The concentration of glucose in the reaction chamber is monitored at periodic intervals using a glucose analyzer of Yellow Spring Instrument, Inc. (YSI). Due to conversion of glucose to ammonium gluconate, 95–100% of glucose as raw material may be converted to ammonium gluconate.

An advantage of the preferred embodiment that uses a glucose concentration at the above described concentrations in the reaction chamber is that enzyme deactivation due to production of small quantities of hydrogen peroxide per unit time is reduced based on the following chemical reaction. Furthermore, due to presence of a relatively large quantity of catalase or equivalent hydrogen peroxide dissociation catalyst, the hydrogen peroxide produced in the reaction is converted to oxygen and water. The three-step reaction process is shown as follows:

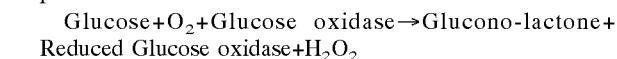
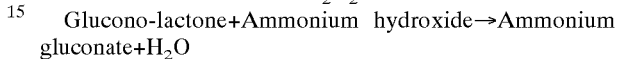
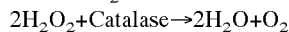

The pH of the reaction mixture is controlled by addition of ammonium hydroxide (10–30%) to maintain the pH of the mixture between pH 4 and 8, for example between pH 5 and 7, for example, between pH 5.5 and 6.5. Regulation of pH facilitates formation of ammonium gluconate. Embodiments of the invention are not intended to be limited to the pH described above. The pH can be modified according to yield performance under a variety of conditions and according to the source and type of catalyst. For example, where catalase is substituted by an insoluble metal, the selected pH as determined by the amount of ammonium hydroxide, may be varied to optimize production of ammonium gluconate. Additionally, enzymes obtained using recombinant microorganisms may operate optimally at pHs that are different from the enzymes isolated from unmodified microorganisms.

An appropriate temperature range of between 15° C. and 40° C. further facilitates ammonium gluconate formation although temperatures outside this range may be used depending on reagent stability. The reaction mixture is sparged continuously with oxygen of atmospheric air and stirred with an agitator as shown in FIG. 1 to ensure proper mixing condition. The pH and temperature of the reaction mixture is preferentially monitored and controlled through an in-built reactor controller.

We have shown for the first time that the conversion of glucose to ammonium gluconate can be achieved economically and efficiently in terms of conversion efficiency of raw material to product using continuous product separation and purification by ultrafiltration membranes. Moreover, this approach provides flexibility with respect to production of other metal gluconates from ammonium gluconate.

Due to continuous reuse of reaction mixture and raw materials and absence of any live microbial and/or fungal organisms the manufacturing process does not generate biological wastes. The effluent discharged from the proposed manufacturing plant meets EPA's regulatory water quality standards without significant waste treatment operations. This proposed process is environmentally friendly and also does not consume enormous local resources to manufacture the final products. The raw materials conversion efficiency is almost 100% due to innovative continuous mode of operations.

In summary, embodiments of the invention include any of continuous production, fed batch and batch preparations for providing a gluconate salt. The gluconate is separated from reactants using ultrafiltration and can be efficiently purified by crystallization. The methods utilize as much as 25–50% less enzyme catalyst mixture compared to prior methods which make the process more cost effective. The methods further may utilize 200–500% less glucose as raw material at any particular time of the operation, which increases the conversion efficiency of raw material to product from the process. The method provides high product concentration and can further provide continuous product separation and purification with a product conversion efficiency of at least 90% and close to 100%.

EXAMPLES

Example 1
Production of Pure Ammonium Gluconate

One gram of Hidelase enzyme was added to the bioreactor reaction mixture containing 3 liters of deionized water. The reactor was then fed with 50% (w/v) glucose solution at a constant feed rate to provide a residual glucose concentration in the 3 liter reaction mixture of about 5% (w/v) for 122 hours. A YSI glucose analyzer was used to measure the residual glucose concentration. The reaction mixture in bioreactor was stirred with an agitator and continuously sparged with air at 3 vvm. The pH of the reaction mixture was maintained between 5.5 and 6.5 by addition of 5–30% (v/v) liquor ammonium hydroxide solution. The temperature of the reaction mixture was maintained between 15–25° C. using a built-in heating and cooling device in the bioreactor assembly. The reaction mixture was continuously circulated through the ultrafiltration membrane (A/G Technology) having a molecular cut-off of 10,000. Under steady state condition the glucose oxidase activity per unit weight of glucose present in the reaction mixture is in the range of between 2 and 20 and the catalase activity per unit weight of glucose present in the reaction mixture is in the range of 50 and 800. Each hundred grams of glucose fed to the reactor produced ammonium gluconate, which was stoichiometrically equivalent to 99% glucose utilized by the reaction mixture. Ammonium gluconate was separated from the permeate stream as shown in FIG. 1 and crystallized to isolate the ammonium gluconate crystals. Due to the absence of any other salts in the reaction mixture these crystals are free from any other impurities.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims. All references cited herein are incorporated by reference.

What is claimed is:

1. A method for preparing metal gluconates, comprising:
   (a) adding a glucose solution to a fluid mixture comprising glucose oxidase in a reaction chamber, adding a metal base to the reaction chamber for forming a reaction mixture containing metal gluconate, and adding air into the reaction chamber;
   (b) removing a portion of the reaction mixture; and
   (c) separating metal gluconate from the portion of the reaction mixture by ultrafiltration;
   wherein the method is carried out by a continuous process.

2. A method according to claim 1, wherein the metal base is a metal base solution.

3. A method according to claim 2, wherein the metal base solution is selected from the group consisting of sodium base, potassium base, calcium base, zinc base, ferrous base, magnesium base, manganese base and cuprous base solution.

4. A method according to claim 2 wherein the portion of the reaction mixture removed from the reaction mixture over a specified period of time comprises an amount of glucose solution added over the specified period of time and an amount of metal base solution added over the specified period of time.

5. A method according to claim 1, wherein the metal base is a metal base suspension.

6. A method according to claim 1 further comprising returning residual reaction mixture into the reaction chamber.

7. A method according to claim 1, wherein the step of ultrafiltration further comprises an ultrafiltration membrane for providing a retentate for returning to the reaction chamber and a permeate containing metal gluconate.

8. A method according to claim 7, further comprising crystallizing metal gluconate from the permeate.

9. A method according to claim 1, wherein glucose oxidase is derived from a micro-organism.

10. A method according to claim 9, wherein the glucose oxidase is obtained from *Aspergillus niger*.

11. A method according to claim 1, wherein the glucose oxidase activity per unit weight of glucose is maintained at less than 20.

12. A method according to claim 1, wherein the fluid mixture further comprises catalase.

13. A method according to claim 12, wherein the catalase is obtained from *Aspergillus niger*.

14. A method according to claim 12, wherein the catalase activity per unit weight of glucose is less than 800.

15. A method according to claim 12 wherein the ratio of glucose oxidase to catalase activity is less than 0.1.

16. A method according to claim 14, wherein the ratio of glucose oxidase to catalase activity is less than 0.1.

17. A method according to claim 1, wherein the reaction chamber is maintained at a temperature of between 15° C. and 40° C.

18. A method according to claim 1, wherein the reaction mixture is maintained at a pH of between 4 and 8.

19. A method according to claim 1, wherein the concentration of glucose in the glucose feed is maintained at less than 75% (w/v).

20. A method according to claim 19, wherein the concentration of glucose in the reaction chamber is maintained at less than 10% (wfv) in the reaction mixture.

21. A method according to claim 8 further comprising reusing residual permeate after separating crystallized metal gluconate from the permeate.

22. A method according to claim 1, wherein ultrafiltration produces a permeate containing metal gluconate, the permeate being substantially environmentally benign.

23. A method for preparing metal gluconates, comprising:
   (a) adding a glucose solution to a preparation comprising glucose oxidase in a reaction chamber and adding a metal base to the reaction chamber for forming a reaction mixture containing metal gluconate, and adding air into the reaction chamber;
   (b) removing a portion of the reaction mixture from the reaction chamber;
   (c) separating a permeate from the portion of the reaction mixture by ultrafiltration; and
   (d) separating metal gluconate from the permeate to form a residual permeate.

24. A method according to claim 23, wherein separating metal gluconate from the permeate includes crystallizing metal gluconate from the permeate.

25. A method according to claim 23 further comprising:

(e) reusing the residual permeate in the reaction chamber.

26. A method according to claim 23, wherein the method is carried out by a continuous process.

27. A method according to claim 23, wherein the preparation is a fluid mixture.

28. A method according to claim 23, wherein the reaction chamber during steady state operation has a ratio of glucose oxidase to grams of glucose of no more than 20.

29. A method according to claim 28, wherein the preparation further comprises catalase.

30. A method according to claim 29, wherein the reaction chamber during steady state operation has a ratio of catalase to grams of glucose of no more than 800.

31. A method according to claim 23, wherein the permeate is substantially environmentally benign.

32. A method for preparing metal gluconates, comprising:

(a) adding a glucose solution to a fluid mixture comprising glucose oxidase in a reaction chamber, and adding a metal base to the reaction chamber for forming a reaction mixture containing metal gluconate, and adding air into the reaction chamber;

(b) removing a portion of the reaction mixture from the reaction chamber; and (c) separating metal gluconate from the portion of the reaction mixture by ultrafiltration;

wherein the reaction chamber during steady state operation has a ratio of glucose oxidase to grams of glucose of no more than 20.

33. A method according to claim 32, wherein the fluid mixture further comprises catalase.

34. A method according to claim 33, wherein the reaction chamber during steady state operation has a ratio of catalase to grams of glucose of no more than 800.

35. A method according to claim 32, wherein the method is carried out by a continuous process.

36. A method according to claim 32, wherein ultrafiltration produces a permeate containing metal gluconate, the permeate being substantially environmentally benign.

37. A method according to claim 32 further comprising:

(d) separating metal gluconate from the permeate to form a residual permeate; and (e) reusing the residual permeate in the reaction chamber.

38. A method for preparing metal gluconates, comprising:

(a) adding a glucose solution to a fluid mixture comprising glucose oxidase in a reaction chamber, and adding a metal base to the reaction chamber for forming a reaction mixture containing metal gluconate, and adding into the reaction chamber;

(b) removing a portion of the reaction mixture from the reaction chamber;

(c) separating a permeate from the portion of the reaction mixture by ultrafiltration, the permeate being substantially environmentally benign;

wherein the method is carried out by a continuous process.

39. A method according to claim 38, wherein the fluid mixture further comprises catalase.

40. A method according to claim 39, wherein the reaction chamber during steady stare operation has a ratio of catalase to grams of glucose of no more than 800.

41. A method according to claim 38 further comprising:

(d) separating metal gluconate from the permeate to form a residual permeate; and (e) reusing the residual permeate in the reaction chamber.

* * * * *

UNITED STATES PATENT AND TRADEMARK OFFICE
CERTIFICATE OF CORRECTION

PATENT NO. : 6,828,130 B2  Page 1 of 1
APPLICATION NO. : 10/142499
DATED : December 7, 2004
INVENTOR(S) : Chinmay Chatterjee et al.

It is certified that error appears in the above-identified patent and that said Letters Patent is hereby corrected as shown below:

Col. 8, line 45
 replace "(wfv)"
 with --(w/v)--.

Col. 10, line 10
 replace "residuaJ"
 with --residual--.

Col. 10, line 15 and 16
replace "adding into"
with --adding air into--

Col. 10, line 26
 replace "stare"
 with --state--.

Signed and Sealed this

Second Day of January, 2007

JON W. DUDAS
*Director of the United States Patent and Trademark Office*